(12) United States Patent
Huang et al.

(10) Patent No.: US 12,259,319 B2
(45) Date of Patent: Mar. 25, 2025

(54) GAS SENSING DEVICE

(71) Applicant: Godsmith Sensor Inc., Taoyuan (TW)

(72) Inventors: Yu-Ren Huang, Taoyuan (TW); Li-Yu Wang, Taoyuan (TW); Ming-Chun Hsiao, Taoyuan (TW); Chun-Han Huang, Taoyuan (TW); Yu-Da Chiu, Taoyuan (TW)

(73) Assignee: GODSMITH SENSOR INC., Taoyuan (TW)

( * ) Notice: Subject to any disclaimer, the term of this patent is extended or adjusted under 35 U.S.C. 154(b) by 196 days.

(21) Appl. No.: 18/319,338

(22) Filed: May 17, 2023

(65) Prior Publication Data

US 2024/0175810 A1    May 30, 2024

(30) Foreign Application Priority Data

Nov. 28, 2022    (TW) .................................. 111145399

(51) Int. Cl.
*G01N 21/3504*    (2014.01)
*G01N 21/31*    (2006.01)

(52) U.S. Cl.
CPC ..... *G01N 21/3504* (2013.01); *G01N 21/3103* (2013.01)

(58) Field of Classification Search
CPC ............. G01N 21/3504; G01N 33/497; G01N 33/4975; G01N 2021/3148; A61B 5/082
See application file for complete search history.

(56) References Cited

FOREIGN PATENT DOCUMENTS

CN          213658572      *    7/2021      ......... G01N 21/3504

* cited by examiner

*Primary Examiner* — David P Porta
*Assistant Examiner* — Meenakshi S Sahu
(74) *Attorney, Agent, or Firm* — HSML P.C.

(57) ABSTRACT

A gas sensing device for detecting a to-be-detected substance in a respiratory gas exhaled by a user includes a housing permitting entrance of the respiratory gas, and a sensing module disposed in the housing. The sensing module includes a light chamber permitting the respiratory gas to pass therethrough, a light source unit emitting light into the light chamber, first and second light sensing units outputting respectively first and second detected signals indicating first and second detected intensities respectively of first and second portions of the light whose wavelengths fall within first and second wavelength ranges, respectively, and a processing unit electrically connected to the first and second light sensing units and determining, based on the first and second detected signals, that the to-be-detected substance exists in the respiratory gas when a difference occurs in each of the first and second detected intensities over time.

8 Claims, 2 Drawing Sheets

GAS SENSING DEVICE

CROSS-REFERENCE TO RELATED APPLICATION

This application claims priority to Taiwanese Invention Patent Application No. 111145399, filed on Nov. 28, 2022.

FIELD

The disclosure relates to a sensing device, and more particularly to a gas sensing device.

BACKGROUND

Currently, invasive measures are undertaken to determine health conditions of patients suffering from diseases such as diabetes. It is necessary for the patients to regularly check their blood glucose, and finger pricks for checking blood glucose cause pain and leave traces on the patients' bodies in the long run. Thus, there is room for improvement on such invasive measures.

SUMMARY

Therefore, an object of the disclosure is to provide a gas sensing device that can alleviate at least one of the drawbacks of the prior art, because monitoring volatile organic compounds (VOCs) from exhaled breath has been used to determine chemical composition of exhaled breath. According to the disclosure, a gas sensing device adapted for detecting a concentration value of a to-be-detected substance in a respiratory gas that is exhaled by a user is provided. Under exposure of light, the to-be-detected substance absorbs a portion of the light having a first absorption wavelength and a second absorption wavelength different from the first absorption wavelength. The gas sensing device includes a housing and a sensing module. The housing has a respiratory gas inlet adapted for entrance of the respiratory gas into the housing. The sensing module is disposed in the housing and includes a chamber a light source unit, a first light sensing unit, a second light sensing unit, and a processing unit. The chamber is adapted to permit the respiratory gas to pass therethrough. The light source unit is configured to emit the light into the chamber. The first light sensing unit includes a first light filter and a first sensor. The first light filter is disposed downstream of the chamber, and is configured to permit passage of a first portion of the light which has passed through the chamber and whose wavelengths fall within a first wavelength range. The first absorption wavelength falls within the first wavelength range. The first sensor is disposed downstream of the first light filter, and is configured to receive the first portion of the light which has passed through the first light filter and to output in real time a first detected signal indicating a first detected intensity of the first portion of the light. The second light sensing unit includes a second light filter and a second sensor. The second light filter is disposed downstream of the chamber, and is configured to permit passage of a second portion of the light which has passed through the chamber and whose wavelengths fall within a second wavelength range. The second absorption wavelength falls within the second wavelength range. The second sensor is disposed downstream of the second light filter, and is configured to receive the second portion of the light which has passed through the second light filter and to output in real time a second detected signal indicating a second detected intensity of the second portion of the light. The processing unit is electrically connected to the first sensor and the second sensor, and is configured to determine based on the first detected signal and the second detected signal received therefrom that the to-be-detected substance exists in the respiratory gas when a difference occurs in each of the first detected intensity and the second detected intensity over time. After the processing unit determines that the to-be-detected substance exists in the respiratory gas, a concentration value of the to-be-detected substance is detected.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
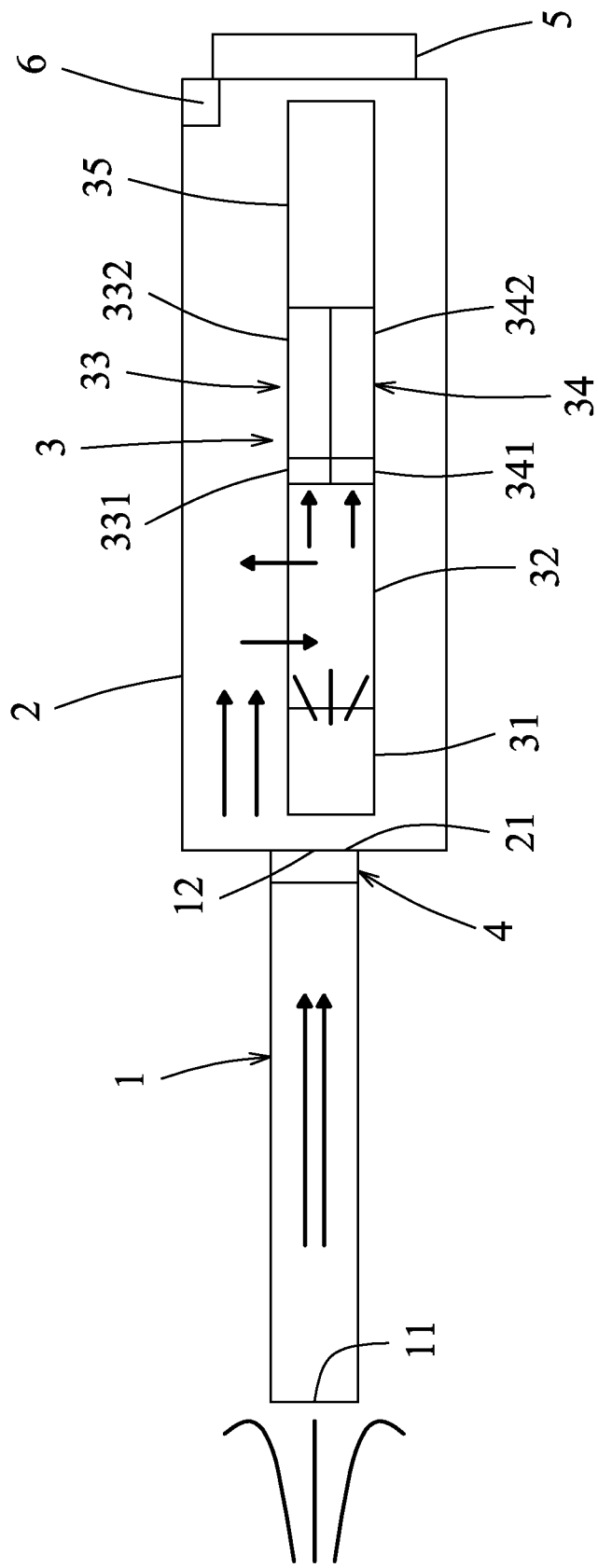
FIG. 1 is a schematic diagram of a gas sensing device of an embodiment according to the present disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

It should be noted herein that for clarity of description, spatially relative terms such as "top," "bottom," "upper," "lower," "on," "above," "over," "downwardly," "upwardly" and the like may be used throughout the disclosure while making reference to the features as illustrated in the drawings. The features may be oriented differently e.g., rotated 90 degrees or at other orientations and the spatially relative terms used herein may be interpreted accordingly.

Figure 2:
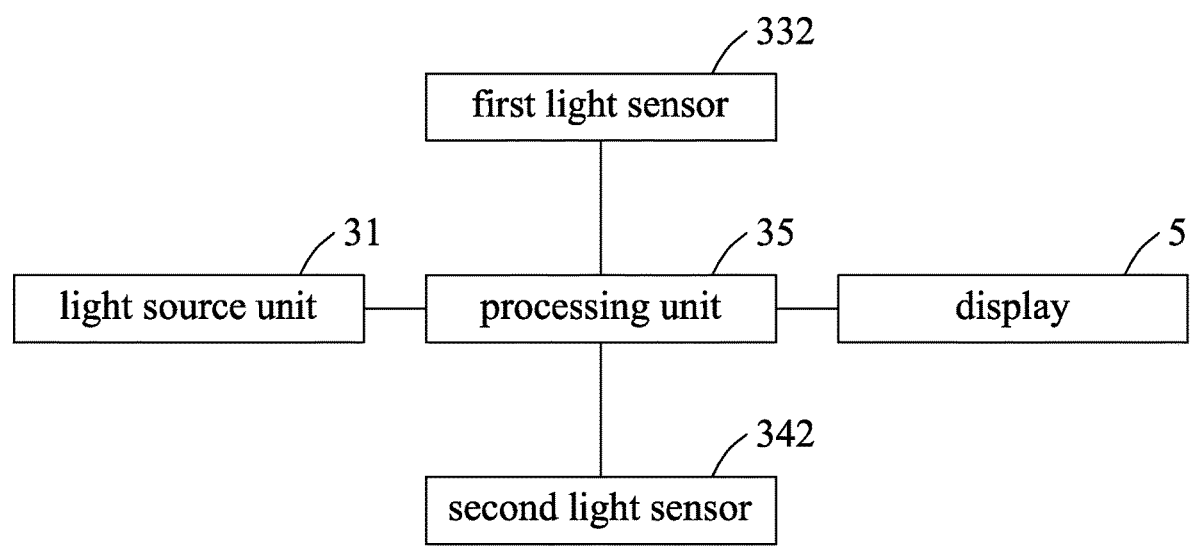
FIG. 2 is a block diagram of the embodiment, illustrating electrical connection among elements of the gas sensing device of the embodiment.

Referring to FIGS. 1 and 2, a gas sensing device of an embodiment according to the present disclosure is adapted for detecting a concentration value of a to-be-detected substance, e.g., acetone, in a respiratory gas that is exhaled by a user, so health conditions of the user, e.g., blood glucose, may be estimated. In this embodiment, the gas sensing device employs infrared light for performing infrared spectroscopy on the respiratory gas to detect the concentration value of the to-be-detected substance. Under the exposure of the infrared light, the to-be-detected substance absorbs a portion of the infrared light having a first absorption wavelength and a second absorption wavelength different from the first absorption wavelength. In this embodiment, the first absorption wavelength falls within a first wavelength range, and the second absorption wavelength falls within a second wavelength range different from the first wavelength range.

The gas sensing device is further adapted for detecting a concentration value of a non to-be-detected substance, e.g., water, that exits in the respiratory gas and that has, under the exposure of the infrared light, a third absorption wavelength falling within the first wavelength range and different from the first absorption wavelength and the second absorption wavelength. Since the third absorption wavelength falls within the first wavelength range, the concentration value of the to-be-detected substance may be affected thereby, a calibration will be conducted on the concentration value of the to-be-detected substance.

The gas sensing device includes a blow tube 1, a housing 2, a sensing module 3, a filtering film 4, a display 5, and a ventilation module 6.

The blow tube 1 is hollow, and includes a collecting portion 11 and a connecting portion 12. The collecting portion 11 is adapted to permit entrance of the respiratory gas into the blow tube 1. The connecting portion 12 is opposite to the collecting portion 11, is connected to the housing 2, and fluidly communicates the collecting portion 11 with the respiratory gas inlet 21 of the housing 2. The arrows shown in FIG. 1 in bold line depict direction of the respiratory gas exhaled by the user.

The housing 2 defines an accommodating space 20 therein and has a respiratory gas inlet 21 adapted for entrance of the respiratory gas into the accommodating space 20 of the housing 2.

The sensing module 3 is disposed in the accommodating space 20 of the housing 2, and includes a light source unit 31, a light chamber 32, a first light sensing unit 33, a second light sensing unit 34, and a processing unit 35.

The filtering film 4 is mounted to the housing 2 and is disposed upstream of the respiratory gas inlet 21. In this embodiment, the filtering film 4 is adapted for filtering out polymer gas in the respiratory gas, and the filtering film 4 may be made of polytetrafluoroethylene (PTFE), but the present disclosure is not limited to this respect.

The display 5 is electrically connected to the processing unit 35, is mounted to the housing 2, and is distal from the respiratory gas inlet 21. In this embodiment, the display 5 is configured to display a final concentration value of the to-be-detected substance and other information such as a concentration value of the non-to-be detected substance.

The ventilation module 6 is mounted to the housing 2, is distal from the respiratory gas inlet 21, and is configured to permit discharge of the respiratory gas in the accommodating space 20. In this embodiment, the ventilation module 6 is an exhaust fan, and the present disclosure is not limited in this respect.

The light source unit 31 is configured to emit the infrared light into the light chamber 32 and may include a plurality of infrared light emitting diodes. In this embodiment, the light source unit 31 is electrically connected to the processing unit 35, is controlled thereby to emit the infrared light, and is powered by a power source (not shown) that is connected to the processing unit 35 and that also provides electricity thereto. In other embodiments, the light source unit 31 is not electrically connected to the processing unit 35, and the light source unit 31 and the processing unit 35 are driven by different power sources. In other embodiments, the light source unit 31 may be configured to emit light that has different wavelengths such as ultraviolet light according to various requirements.

The light chamber 32 fluidly communicates with the accommodating space 20 and is adapted to permit the respiratory gas to pass therethrough. The infrared light emitted by the light source unit 31 illuminates the respiratory gas in the light chamber 32 and is propagated to the first light sensing unit 33 and the second light sensing unit 34.

Specifically, the first light sensing unit 33 and the second light sensing unit 34 are disposed downstream of the light chamber 32 and are electrically connected to the processing unit 35.

The first light sensing unit 33 includes a first light filter 331 and a first light sensor 332. The first light filter 331 is disposed downstream of the light chamber 32, and is configured to permit passage of a first portion of the infrared light which has passed through the light chamber 32 and whose wavelengths fall within the first wavelength range. It should be noted that the first absorption wavelength falls within the first wavelength range. The first light sensor 332 is disposed downstream of the first light filter 331, and is configured to receive the first portion of the infrared light which has passed through the first light filter 331 and to output in real time a first detected signal indicating a first detected intensity of the first portion of the infrared light.

The second light sensing unit 34 includes a second light filter 341 and a second light sensor 342. The second light filter 341 is disposed downstream of the light chamber 32, and is configured to permit passage of a second portion of the infrared light which has passed through the light chamber 32 and whose wavelengths fall within the second wavelength range. It should be noted that the second absorption wavelength falls within the second wavelength range. The second light sensor 342 is disposed downstream of the second light filter 341, and is configured to receive the second portion of the infrared light which has passed through the second light filter 341 and to output in real time a second detected signal indicating a second detected intensity of the second portion of the infrared light. In this way, only the first portion and second portion of the infrared light whose wavelengths falling respectively within the first wavelength range and the second wavelength range are permitted to pass through the first light filter 331 and the second light filter 341, and the remaining portion of the infrared light whose wavelengths falling out of the first wavelength range and the second wavelength range would not affect determination of the concentration value of the to-be-detected substance. In addition, carbon dioxide and other common chemical substances existed in the light chamber 32 do not absorb the infrared light that is emitted from the light source unit 31, and thus the first portion and the second portion of the infrared light which have passed through the light chamber 32 would not be affected and are respectively received by the first light sensor 332 and the second light sensor 342 without loss. Thus, it is advantageous to employ infrared light as a light source in this embodiment.

The processing unit 35 is electrically connected to the first sensor 332 and the second sensor 342 and is configured to determine, based on the first detected signal and the second detected signal received therefrom, that the to-be-detected substance exists in the respiratory gas when a difference occurs in each of the first detected intensity and the second detected intensity over time. The processing unit 35 stores a conversion data, a comparison data, and a calibration data.

The conversion data includes a plurality of first concentration values of the to-be-detected substance, a plurality of first intensities that are associated respectively with the first concentration values, a plurality of second concentration values of the to-be-detected substance, and a plurality of second intensities that are associated respectively with the second concentration values.

The comparison data includes a plurality of third concentration values of the non to-be-detected substance and a plurality of third intensities that are associated respectively with the third concentration values. The calibrating data includes a plurality of fourth concentration values and a plurality of calibrating values that are related to the concentration value of the to-be-detected substance and that are associated respectively with the fourth concentration values.

A procedure for detecting the concentration value of the to-be-detected substance in the respiratory gas of the present disclosure is described in the following.

It should be noted that, in the embodiment of the present embodiment, the to-be-detected substance is acetone, the first absorption wavelength is 7.3 μm, the second absorption wavelength is 8.3 μm, the first wavelength range ranges from 7.1 μm to 7.5 μm, and the second wavelength range ranges from 8.1 μm to 8.5 μm. On the other hand, the non to-be-detected substance is water, and has the third absorption wavelength falling within a wavelength range ranging from 5 μm to 8 μm within which the first wavelength range falls. As a result, water in the respiratory gas absorbs a portion of the infrared light having the third absorption wavelength and affects an amount of the infrared light whose wavelengths fall within the first wavelength range being absorbed by the to-be-detected substance, i.e., acetone, in the respiratory gas. In this embodiment, the conversion data includes the first concentration values of acetone that are associated respectively with the first intensities of the infrared light within the first wavelength range (e.g., a voltage value or a current value converted from an intensity of the infrared light) and the second concentration values of acetone that are associated respectively with the second intensities of the infrared light within the second wavelength range. The comparison data includes the third concentration values of water that are associated respectively with the third intensities of the infrared light (e.g., a voltage value or a current value converted from an intensity of the infrared light). The calibrating data includes the fourth concentration values of water that are associated respectively with the calibrating values for calibrating the concentration value of acetone.

To detect a concentration value of the to-be-detected substance, the gas sensing device is first turned on, and a user exhales a respiratory gas that flows into the blow tube 1 via the collecting portion 11, that is filtered by the filtering film 4, and that flows into the accommodating space 20 via the connecting portion 12 to enter the light chamber 32.

Under the exposure of the infrared light emitted by the light source unit 31, acetone in the respiratory gas absorbs a portion of the infrared light having the first absorption wavelength and the second absorption wavelength, water in the respiratory gas absorbs another portion of the infrared light having the third absorption wavelength, and substance other than acetone and water in the respiratory gas absorbs still another portion of the infrared light having a absorption wavelength of that substance.

Then, the first light filter 331 permits passage of the first portion of the infrared light whose wavelengths fall within the first wavelength range and that is to be received by the first light sensor 332. The first light sensor 332 outputs in real time the first detected signal that indicates the first detected intensity of the first portion of the infrared light and that is to be received by the processing unit 35. Similarly, the second light filter 341 permits passage of the second portion of the infrared light whose wavelengths fall within the second wavelength range and that is to be received by the second light sensor 342. The second light sensor 342 outputs in real time the second detected signal that indicates the second detected intensity of the second portion of the infrared light and that is to be received by the processing unit 35. In this way, concentration of the to-be-detected substances in the respiratory gas that have the first absorption wavelength falling within the first wavelength range and the second absorption wavelength falling within the second wavelength range may be estimated according to the first detected signal and the second detected signal.

The processing unit 35 determines that the to-be-detected substance, i.e., acetone, exists in the respiratory gas when a difference occurs in each of the first detected intensity and the second detected intensity over time. Since the to-be-detected substance absorbs the portion of the infrared light having the first absorption wavelength and another portion of the infrared light having the second absorption wavelength, the concentration value of the to-be-detected substance may be analyzed more accurately according to the first detected signal and the second detected signal. It should be noted that more light sensing units that include a light sensor and a light filter permitting passage of a portion of the infrared light whose wavelengths fall within a wavelength range different from the first wavelength range and the second wavelength range may be employed to more accurately analyze the concentration of the to-be-detected substance. Since specifics of analyzing the concentration of the to-be-detected substance are known in the field of infrared spectroscopy, further details of the same are omitted for the sake of brevity.

Specifically, when the processing unit 35 determines that the to-be-detected substance exists in the respiratory gas, the processing unit 35 further determines, upon receipt of the first detected signal, one of the first concentration values associated with one of the first intensities that matches the first detected intensity as a first detected concentration value of the to-be-detected substance, and determines, upon receipt of the second detected signal, one of the second concentration values associated with one of the second intensities that matches the second detected intensity as a second detected concentration value of the to-be-detected substance. Then, the processing unit 35 outputs either one of the first detected concentration value and the second detected concentration value as a final concentration value of the to-be-detected substance when the first detected concentration value is equal to the second detected concentration value. In this case, only the to-be-detected substance is detected in the respiratory gas and the display 5 displays the final concentration value of the to-be-detected substance. It should be noted that in other embodiments, the processing unit 35 may output either one of the first detected concentration value and the second detected concentration value as the final concentration value of the to-be-detected substance when a difference between the first detected concentration value and the second detected concentration value is smaller than a predetermined value. In this embodiment, the first and second concentration values of the to-be-detected substance are in negative correlation with the first and second intensities. The first detected concentration value and the second detected concentration value of the to-be-detected substance can be thus determined by the processing unit 35 according to the conversion data.

On the other hand, in a case where the first detected concentration value is not equal to the second detected concentration value, such situation represents that some substance other than acetone exists in the respiratory gas and affects the first detected intensity of the first detected signal, so calibration on the first detected concentration value needs to be conducted. At this time, the processing unit 35 further determines, when the first detected concentration value is not equal to the second detected concentration value, one of the third concentration values associated with one of the third intensities that matches the first detected intensity as a third detected concentration value of the non to-be-detected substance, i.e., water in this embodiment. When acetone and water both exist in the respiratory gas, since the first absorption wavelength of acetone and the third absorption wavelength of water both fall within the first wavelength range, acetone and water absorb both a portion of the infrared light having the first absorption wavelength and the third absorption wavelength. Consequently, the first detected intensity of the first detected signal is decreased (as compared to a case where only acetone exists in the respiratory gas) and the first detected concentration value thus determined is greater than an actual concentration value of acetone in the respiratory gas. That is to say, water in the respiratory gas is incorrectly identified as acetone in the respiratory gas. Then, the processing unit 35 calibrates the first detected concentration value based on one of the calibrating values associated with one of the fourth concentration values that matches the third detected concentration value to obtain a first calibrated concentration value. In this embodiment, the first calibrated concentration value is obtained by subtracting said one of the calibrating values that matches the third detected concentration value from the first detected concentration value. It should be noted that since the second absorption wavelength and the third absorption wavelength fall within different wavelength ranges, water in the respiratory gas will not absorb the infrared light having the second absorption wavelength, and the second detected intensity is not affected thereby. In other embodiments, the manner for calibrating the first calibrated concentration value may be varied according to different requirements. Subsequently, the processing unit 35 outputs either one of the first calibrated concentration value and the second detected concentration value as the final concentration value of the to-be-detected substance when the first calibrated concentration value is equal to the second detected concentration value. Finally, the display 5 displays the final concentration value received from the processing unit 35, and the respiratory gas is discharged out of the accommodating space 20 by the ventilation module 6. In this way, the health condition, e.g., blood glucose, of the user may be estimated and monitored based on the final concentration value of acetone.

It should be noted that in case where the first calibrated concentration value is not equal to the second detected concentration value, then the processing unit 35 outputs a warning signal. In this embodiment, the warning signal indicates that there may be an unknown substance other than water and acetone existed in the respiratory gas and that an absorption wavelength of the unknown substance falls within one of or both of the first wavelength range and the second wavelength range. The warning signal may represent some abnormal situations that should be taking care of and the present disclosure is not limited in this respect. It should be noted that, the processing unit 35 is a microcontroller or a controller such as, but not limited to, a single core processor, a multi-core processor, a dual-core mobile processor, a microprocessor, a microcontroller, a digital signal processor (DSP), a field-programmable gate array (FPGA), an application specific integrated circuit (ASIC), a radio-frequency integrated circuit (RFIC), etc.

In summary, by virtue of the sensing module 3 of the embodiment, the final concentration value of the to-be-detected substance may be obtained by blowing respiratory gas into to the gas sensing device by the user. In this way, a non-invasive measure for determining the health conditions of the user may be carried out. Furthermore, since the final concentration value is obtained based on the first detected signal and the second detected signal respectively indicating the first detected intensity and the second detected intensity of the infrared light whose wavelengths fall respectively within the first wavelength range and the second wavelength range, a more accurate estimation may be achieved. Additionally, in case where the non to-be-detected substance, such as water, that has the third absorption wavelength falling within the first wavelength range, exists in the respiratory gas, calibration on the first detected concentration value is conducted by deducting said one of the calibrating values that matches the third detected concentration value from the first detected concentration value as referring to the comparison data and the calibration data. In this way, even if there is substance other than the to-be-detected substance exist in the respiratory gas, the gas sensing device of the present disclosure may also obtain a relative accurate concentration value of the to-be-detected substance, and the purpose of this disclosure is achieved.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A gas sensing device adapted for detecting a concentration value of a to-be-detected substance in an respiratory gas that is exhaled by a user, under exposure of light, the to-be-detected substance absorbing a portion of the light having a first absorption wavelength and a second absorption wavelength different from the first absorption wavelength, said gas sensing device comprising:
   a housing that has a respiratory gas inlet adapted for entrance of the respiratory gas into said housing; and
   a sensing module that is disposed in said housing, and that includes
      a light chamber adapted to permit the respiratory gas to pass therethrough,
      a light source unit configured to emit the light into said light chamber, a first light sensing unit including
  a first light filter that is disposed downstream of said light chamber, and that is configured to permit passage of a first portion of the light which has passed through said light chamber and whose wavelengths fall within a first wavelength range, the first absorption wavelength falling within the first wavelength range; and
  a first sensor that is disposed downstream of said first light filter, and that is configured to receive the first portion of the light which has passed through said first light filter and to output in real time a first detected signal indicating a first detected intensity of the first portion of the light,
a second light sensing unit including
  a second light filter that is disposed downstream of said light chamber, and that is configured to permit passage of a second portion of the light which has passed through said light chamber and whose wavelengths fall within a second wavelength range different from the first wavelength range, the second absorption wavelength falling within the second wavelength range, and
  a second sensor that is disposed downstream of said second light filter, and that is configured to receive the second portion of the light which has passed through said second light filter and to output in real time a second detected signal indicating a second detected intensity of the second portion of the light, and
a processing unit electrically connected to said first sensor and said second sensor, and configured to determine, based on the first detected signal and the second detected signal received therefrom, that the to-be-detected substance exists in the respiratory gas when a difference occurs in each of the first detected intensity and the second detected intensity over time.

2. The gas sensing device as claimed in claim 1, wherein said processing unit stores a conversion data including a plurality of first concentration values of the to-be-detected substance, a plurality of first intensities that are associated respectively with the first concentration values, a plurality of second concentration values of the to-be-detected substance, and a plurality of second intensities that are associated respectively with the second concentration values, said processing unit being configured to:
  determine, upon receipt of the first detected signal, one of the first concentration values associated with one of the first intensities that matches the first detected intensity as a first detected concentration value of the to-be-detected substance;
  determine, upon receipt of the second detected signal, one of the second concentration values corresponding to one of the second intensities that matches the second detected intensity as a second detected concentration value of the to-be-detected substance; and
  output either one of the first detected concentration value and the second detected concentration value as a final concentration value of the to-be-detected substance when the first detected concentration value is equal to the second detected concentration value.

3. The gas sensing device as claimed in claim 2, further adapted for detecting a concentration value of a non to-be-detected substance that is in the respiratory gas and that absorbs, under exposure of the light, a portion of the light having a third absorption wavelength that falls within the first wavelength range and that is different from the first absorption wavelength and the second absorption wavelength, wherein:
  said processing unit stores a comparison data including a plurality of third concentration values of the non to-be-detected substance and a plurality of third intensities that are associated respectively with the third concentration values, and a calibrating data including a plurality of fourth concentration values and a plurality of calibrating values that are related to the concentration value of the to-be-detected substance and that are associated respectively with the fourth concentration values; and
  said processing unit is further configured to
  determine, when the first detected concentration value is not equal to the second detected concentration value, one of the third concentration values associated with one of the third intensities that matches the first detected intensity as a third detected concentration value of the non to-be-detected substance existing in the respiratory gas,
  calibrate the first detected concentration value based on one of the calibrating values associated with one of the fourth concentration values that matches the third detected concentration value to obtain a first calibrated concentration value, and
  output either one of the first calibrated concentration value and the second detected concentration value as the final concentration value of the to-be-detected substance when the first calibrated concentration value is equal to the second detected concentration value.

4. The gas sensing device as claimed in claim 3, wherein said processing unit is configured to output a warning signal when the first calibrated concentration value is different from the second detected concentration value.

5. The gas sensing device as claimed in claim 3, the to-be-detected substance being acetone, the non to-be-detected substance being water, the first wavelength range ranging from 7.1 μm to 7.5 μm, and the second wavelength range ranging from 8.1 μm to 8.5 μm, wherein said processing unit stores the conversion data including the first concentration values of acetone that are associated respectively with the first intensities of the light within the first wavelength range and the second concentration values of acetone that are associated respectively with the second intensities of the infrared light within the second wavelength range, the comparison data including the third concentration values of water that are associated respectively with the third intensities of the light at the third absorption wavelength within the first wavelength range, and the calibrating data including the fourth concentration values of water that are associated respectively with the calibrating values for calibrating the concentration value of acetone.

6. The gas sensing device as claimed in claim 1, further comprising a filtering film mounted to said housing and disposed upstream of said respiratory gas inlet and adapted for filtering out polymer gas in the respiratory gas.

7. The gas sensing device as claimed in claim 1, further comprising a display electrically connected to said processing unit, mounted to said housing, being distal from said respiratory gas inlet, and configured to display the final concentration value of the to-be-detected substance.

8. The gas sensing device as claimed in claim 1, further comprising a blow tube that is hollow and that includes:
  a collecting portion adapted to permit entrance of the respiratory gas into said blow tube; and a connecting portion opposite to said collecting portion, connected to said housing, and fluidly communicating said collecting portion with said respiratory gas inlet of said housing.

* * * * *